United States Patent [19]

Fitzpatrick

[11] Patent Number: 5,016,619
[45] Date of Patent: May 21, 1991

[54] MASSAGING DEVICE

[76] Inventor: Margaret Fitzpatrick, 11 Thomas Ct., San Mateo, Calif. 94401

[21] Appl. No.: 439,152

[22] Filed: Nov. 20, 1989

[51] Int. Cl.$^5$ .............................................. A61H 7/00
[52] U.S. Cl. ...................................... 128/67; 128/44; 128/62 R; 128/65; 15/104.94
[58] Field of Search .................. 128/44, 59, 60, 61, 128/62 R, 65, 67; 15/104.94, 227

[56] References Cited

U.S. PATENT DOCUMENTS

| | | | |
|---|---|---|---|
| 874,251 | 12/1907 | Schelling | 128/62 R |
| 2,711,731 | 6/1955 | Krohne | 128/67 |
| 3,959,841 | 6/1976 | Hornel . | |
| 4,091,491 | 5/1978 | Hoffman . | |
| 4,249,521 | 2/1981 | Gueret . | |
| 4,505,271 | 3/1985 | Weber . | |
| 4,667,659 | 5/1987 | Hayday | 128/62 R |
| 4,892,091 | 1/1990 | Sullenger | 128/62 R |

Primary Examiner—Richard J. Apley
Assistant Examiner—Linda C. Maas Dvorak
Attorney, Agent, or Firm—Leon Gilden

[57] ABSTRACT

A massaging device is set forth wherein a support shaft includes a matrix of relatively soft bristles extending therefrom. The shaft includes a handle selectively mounted thereto, wherein an alternative handle may be utilized to accommodate an extension to enable directing of the device to a further extent interiorly between a cast and a skin surface. Modifications of the device include variable stiffness of bristles mounted within the shaft, wherein a further embodiment includes a bristle accessory threadedly received within a forward end of a conduit to receive lotion to direct the lotion onto the skin surface to minimize itching and scaling of the skin surface.

2 Claims, 4 Drawing Sheets

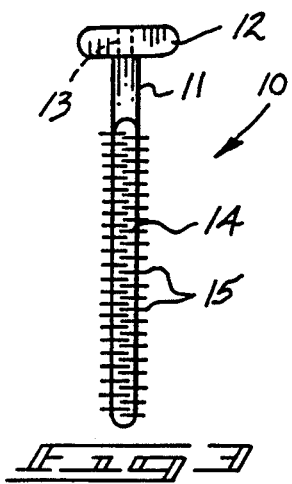
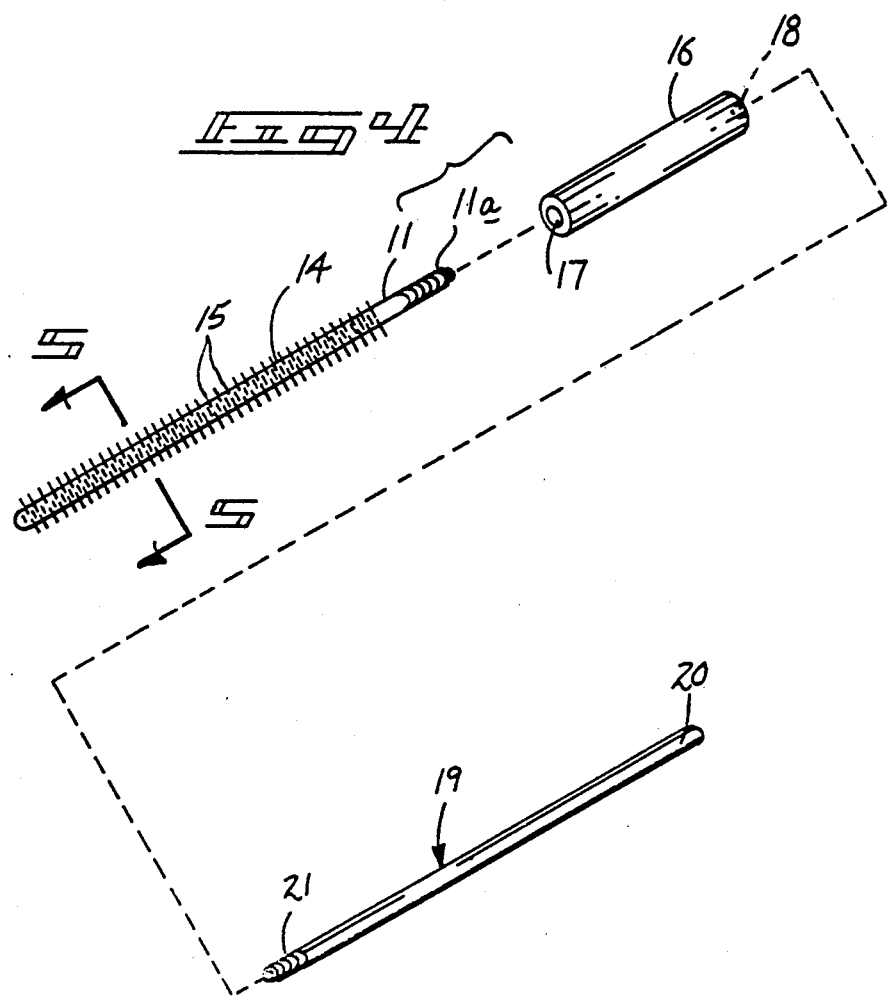

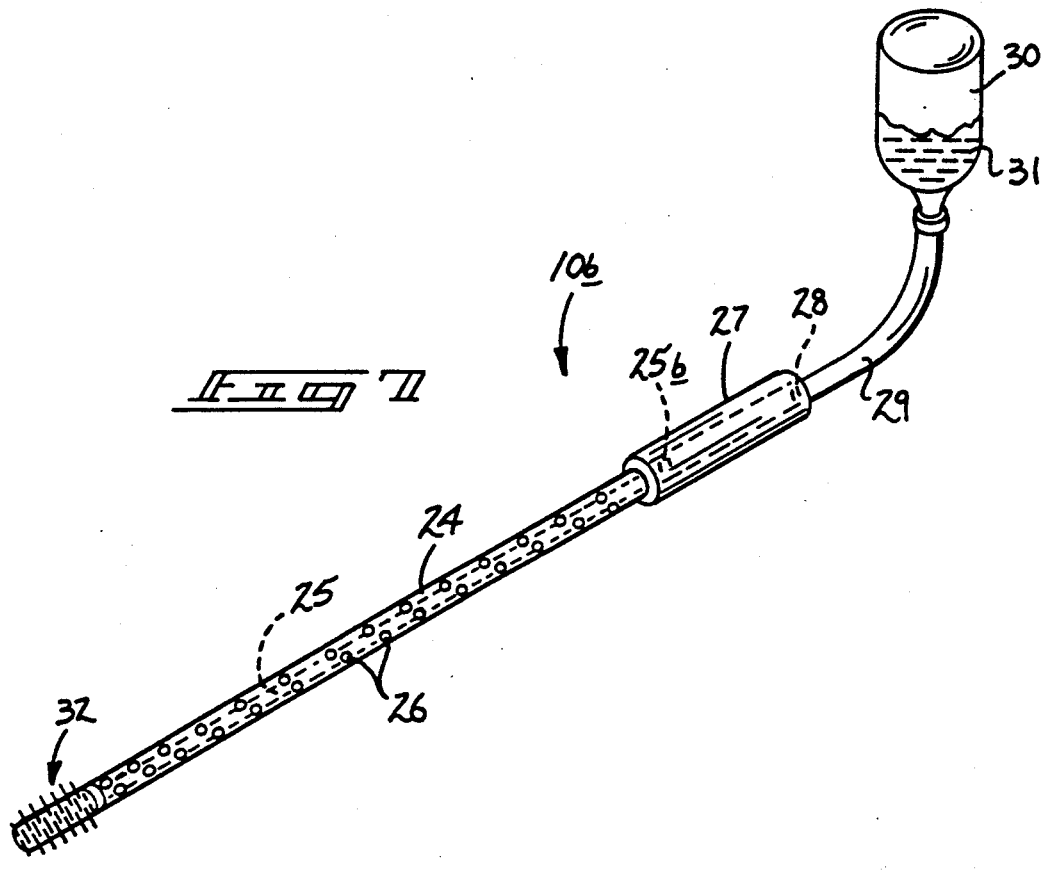
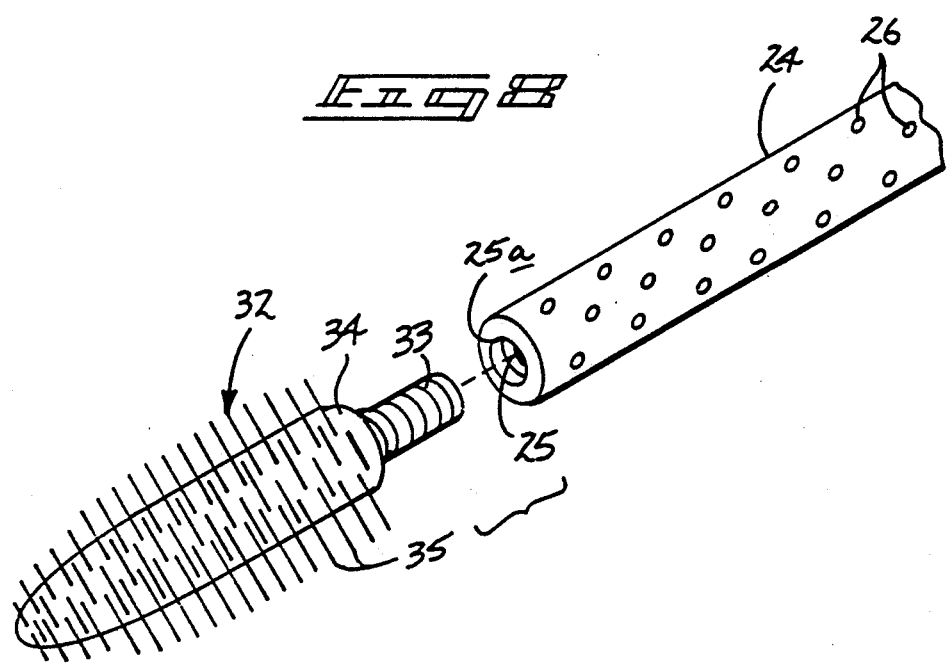

MASSAGING DEVICE

BACKGROUND OF THE INVENTION

1. Field of the Invention

The field of invention relates to massaging devices, and more particularly pertains to a new and improved massaging device wherein the same enables a massaging of a skin surface underlying a cast.

2. Description of the Prior Art

Subsequent to a facture of an appendage by an individual, a cast is frequently mounted thereover for a prolonged period of time. Due to the extended period of time an individual utilizes a cast, the underlying skin surface becomes subject to scaling with attendant discomfort. The prior art has attempted to provide various devices to accommodate and effect a massaging of the skin surface to relieve discomfort. Such a device may be found in U.S. Pat. No. 4,667,659 to Hayday wherein an elongate, rigid planar rod, including a looped handle which includes a series of protrusions directed outwardly of the handle and surface to enable a massaging of the skin.

U.S. Pat. No. 3,959,841 to Horne sets forth a device for applying a lotion to a skin wherein looped ends directed at terminal end portions of a folded fabric is provided to receive a packet to enable directing of fluid therefrom onto a skin surface.

U.S. Pat. No. 4,249,521 to Gueret provides a massaging implement configured as a brush, wherein the brush includes a pad with discontinuous spaced fingers or barbs to effect massaging of a surface.

U.S. Pat. No. 4,505,721 to Weber sets forth a laminar construction of plural elastic fiber layers held together at the longitudinal edges by elastic joints wherein the device is wrapped around a body portion to be treated.

U.S. Pat. No. 4,091,491 to Hoffman sets forth a skin care device configured as a mitt for securement overlying a hand to enable cleansing and massaging of the skin by use of the mitt directed over a skin surface.

As such, it may be appreciated that there is a continuing need for a new and improved massaging device wherein the same addresses both the problems of ease of use and effectiveness in construction and in this respect, the present invention substantially fulfills this need.

SUMMARY OF THE INVENTION

In view of the foregoing disadvantages inherent in the known types of massaging devices now present in the prior art, the present invention provides a massaging device wherein the same is selectively directed to a skin surface between a cast and the skin surface to effect massaging and selective application of lotion thereto. As such, the general purpose of the present invention, which will be described subsequently in greater detail, is to provide a new and improved massaging device which has all the advantages of the prior art massaging devices and none of the disadvantages.

To attain this, the massaging device of the instant invention comprises an elongate, relatively rigid polymeric rod formed with a threaded upper end receivable within a handle. The rod includes a smooth upper portion and a bristled lower portion approximately tow-thirds of the rod. The rod is further selectively securable to a cylindrical handle that in turn receives an extension handle to enable directing of the messaging bristles to an increased depth within the cast overlying a skin surface. Optionally, the bristles may be of a dual length and rigidity to provide a varied massaging action on a skin surface. A further modification of the device includes a bristle member threadedly mounted to an apertured conduit to enable directing of a fluid to the conduit and onto the skin surface, wherein the brush surface enhances directing and application of the fluid, as well as massaging the skin surface in use.

My invention resides not in any one of these features per se, but rather in the particular combination of all of them herein disclosed and claimed and it is distinguished from the prior art in this particular combination of all of its structures for the functions specified.

These has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is i intended to be limiting as to the scope of the invention in any way.

It is therefore an object of the present invention to provide a new and improved massaging device which as all the advantages of the prior art massaging devices and none of the disadvantages.

It is another object of the present invention to provide a new and improved massaging device which may be easily and efficiently manufactured and marketed.

It is a further object of the present invention to provide a new and improved massaging device which is of a durable and reliable construction.

An even further object of the present invention is to provide a new and improved massaging device which is susceptible of a low cost of manufacture with regard to both materials and labor, and which accordingly is then susceptible of low prices of sale to the consuming public, thereby making such massaging devices economically available to the buying public.

Still yet another object of the present invention is to provide a new and improved massaging device which provided in the apparatuses and methods of the prior art some of the advantages thereof, while simultaneously overcoming some of the disadvantages normally associated therewith.

Still another object of the present invention is to provide a new and improved massaging device wherein the same is directed onto a skin surface underlying a cast to effect massaging and optional lotion application thereto.

These together with other objects of the invention, along with the various features of novelty which characterize the invention, are pointed out with particularity in the claims annexed to and forming a part of this disclosure. For a better understanding of the invention, its operating advantages and the specific objects attained by it uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic view taken in elevation of the instant invention.

FIG. 4 si an isometric illustration, somewhat exploded, of the instant invention utilizing an optional handle extension.

FIG. 7 is an isometric illustration of a further modified massaging device of the instant invention.

FIG. 8 is an isometric illustration, somewhat exploded, of the brush and apertured tube in association of the invention as illustrated in FIG. 7.

DESCRIPTION OF THE PREFERRED EMBODIMENT

Figure 1:
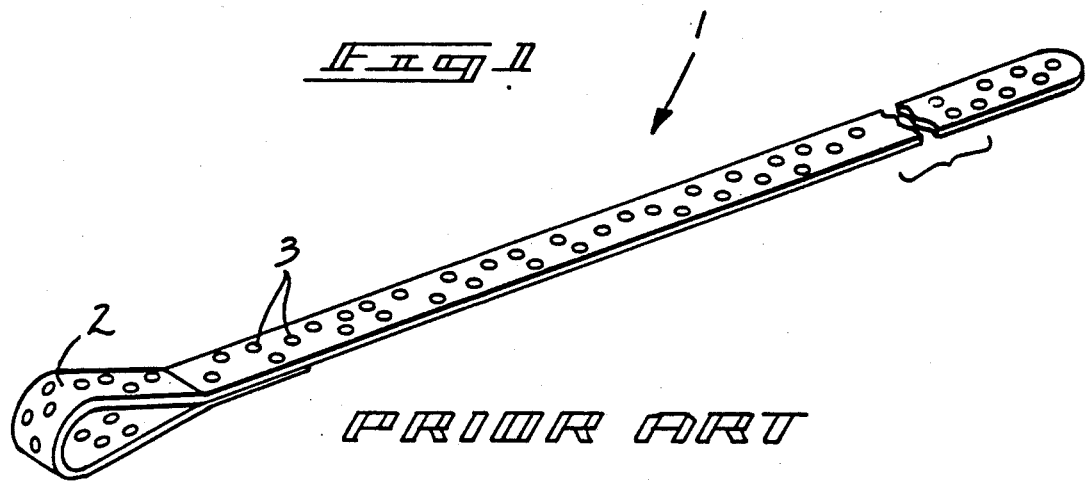
FIG. 1 is an isometric illustration of a prior art device.

With reference now to the drawings, and in particular to FIGS. 1 to 8 thereof, a new and improved massaging device embodying the principles and concepts of the present invention and generally designated by the reference numerals 10, 10a, and 10b will be described.

Figure 2:
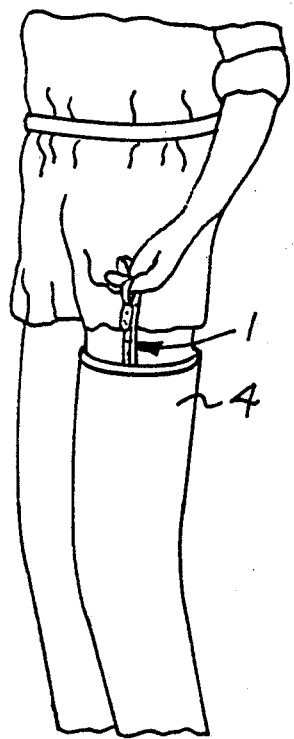
FIG. 2 is an isometric illustration of the prior art device of FIG. 1 in use.

More specifically, the massaging device 10 of the instant invention essentially comprises an improvement over the prior art devices, as illustrated in FIG. 1, wherein an elongate, planar support member includes a series of projections 3 mounted thereon with a looped handle 2 formed at an upper terminal end of the device. The device is utilized to effect massaging between a cast 4 and underlying skin, as illustrated in FIG. 2.

The massaging device 10 is formed with an elongate cylindrical rod 11 with a handle 12 formed with an apertured bore 13 to receive an upper threaded end of the rod 11. The rod 11 includes a bristled lower surface 14 including a matrix of relatively soft bristles extending therefrom to cover at least two-third the surface of the rod 11 providing a smooth surface between the bristles and the handle 12 to minimize unwarranted massaging of an individual's hand secured about the handle 12 in use.

FIG. 4 is illustrative of the instant invention utilizing an accessory cylindrical handle 16 formed with a through-extending threaded bore 17 formed with an end portion 18 to threadedly receive a forward threaded handle extension portion 21 of a handle extension 19. The handle extension 19 includes a smooth exterior shaft portion 20 for grasping by an individual. The rod 11 is accordingly threadingly received coaxially within the threaded bore 17 at a forward end of the handle 16 to provide an elongated massaging device wherein an individual may direct massaging at greater depths between a cast and underlying skin surface in a manner as illustrated in FIG. 2.

Figure 5:
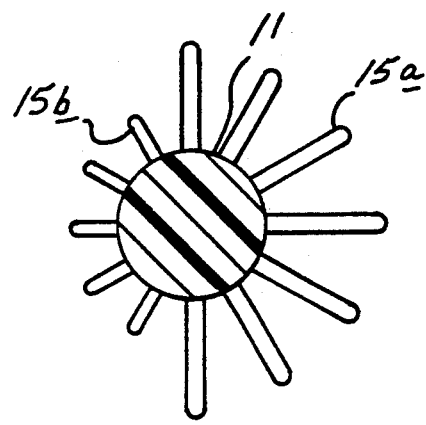
FIG. 5 is an orthographic view taken along the lines 5—5 of FIG. 4 in the direction indicated by the arrows.

FIG. 5 illustrates the use of a bristle matrix wherein long rigid bristles 15a are formed about a semi-spherical surface of the rod 11 with short soft bristles 15b mounted at the opposing semi-spherical surface area of the rod 11 to provide a varied texture to enhance massaging of a skin surface in use.

Figure 6:
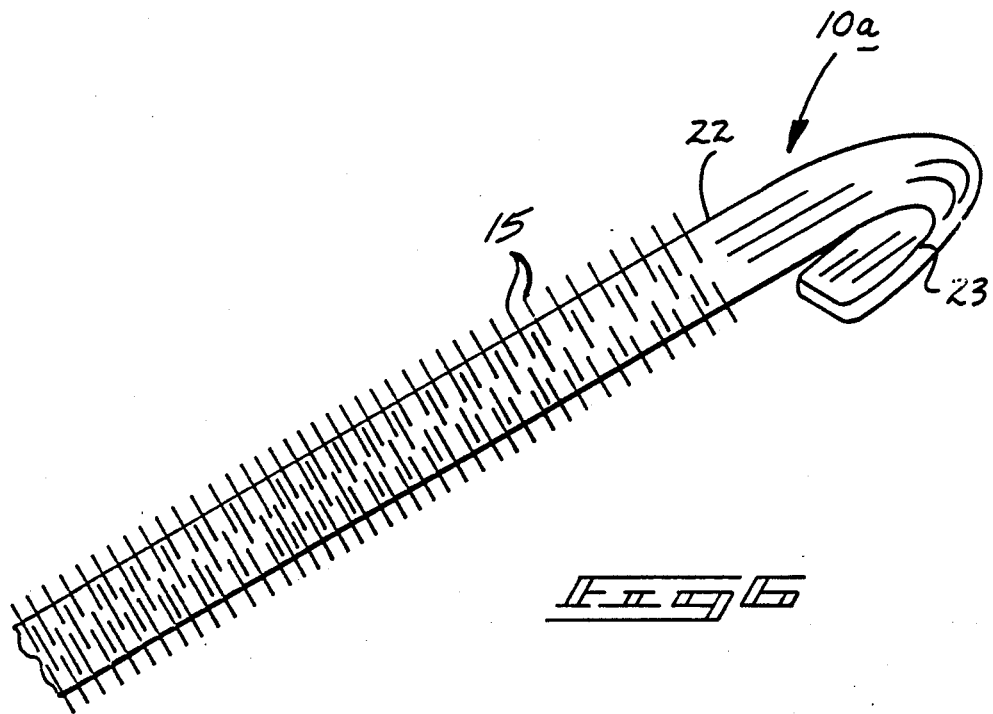
FIG. 6 is an isometric illustration of a modified massaging device of the instant invention.

FIG. 6 illustrates a modified massaging device 10 wherein the bristles 15 mounted orthogonally and exteriorly relative to a cylindrical shaft 22 formed with an integral hooked handle member 23 as the hooked handle portion prevents directing of the modified massaging device 10a completely underlying the cast 4 in use as the hook portion 23 will overlie the cast during a projection of the device 10a in a massaging procedure.

FIG. 7 is illustrative of a further modified massaging device 10b wherein an apertured shaft 24 is formed with a central conduit 25 including an internally threaded forward ned 25a and an externally threaded rearward end 25b to respectively secure a brush member 32 within the forward end of the apertured shaft 24 and to threadedly secure the rearward portion, including the rear threaded end 25b within a cylindrical handle 27 formed with a through-extending threaded bore coaxially of the handle 27, wherein the threaded handle bore 28 threadedly receives a fluid tube 29 at a rear ward portion of the handle 27, wherein the fluid tube 29 is secured in fluid communication with a fluid reservoir 30 containing a quantity of fluid lotion 31 therewithin to enable directing of the fluid lotion through the fluid tube 29 and proceeding through the threaded handle bore 28 and into the central conduit 25 of the apertured shaft 24, wherein the fluid is directed onto a skin surface through the dispensing ports 26 that are in fluid communication with the central conduit 25. The brush member 32 is formed with a threaded boss 33 to be received within the threaded forward end 25a and includes a fabric sheath 34 in surrounding relationship of the surface of the brush member 32 with the bristles 35 projecting thereof, wherein the fabric sheath enhances absorption and application of lotion throughout a skin surface and wherein the bristles 35 effect a massaging of the skin to alleviate irritation and discomfort thereof.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A massaging device organization comprising, in combination,
    an elongate cylindrical shaft including a matrix of bristles directed exteriorly of an external surface defined by the shaft, wherein the bristles extend over a major portion of the shaft from a forward terminal end of the shaft rearwardly thereof, and
    a handle selectively securable to an upper terminal end of the shaft, wherein a smooth surface is defined by the shaft between the handle and the major portion of the shaft to prevent undesirable projection of the bristles with an individual's hand secured about the handle, and
    including a further handle defined by an elongate cylinder with a through-extending bore directed coaxially through the further handle, and the further handle threadedly securable to the upper terminal end of the shaft, and a further rod handle securable to the further handle in coaxial alignment with the shaft and the further handle, and wherein the further rod handle includes a forward threaded end receivable within the further handle remote from the shaft, wherein the further handle is securable to the shaft upon disengagement of the handle relative to the shaft.

2. A massaging device organization as set forth in claim 1 wherein the bristles include a first series of bristles formed about a semi-cylindrical portion of the exterior surface of the shaft of a first rigidity, and further including a second series of bristles formed about a remaining semi-cylindrical surface of the shaft of a second rigidity, wherein the second series of bristles are shorter than the first bristles and wherein the second rigidity is less than the first rigidity.

* * * * *